Figure 4:
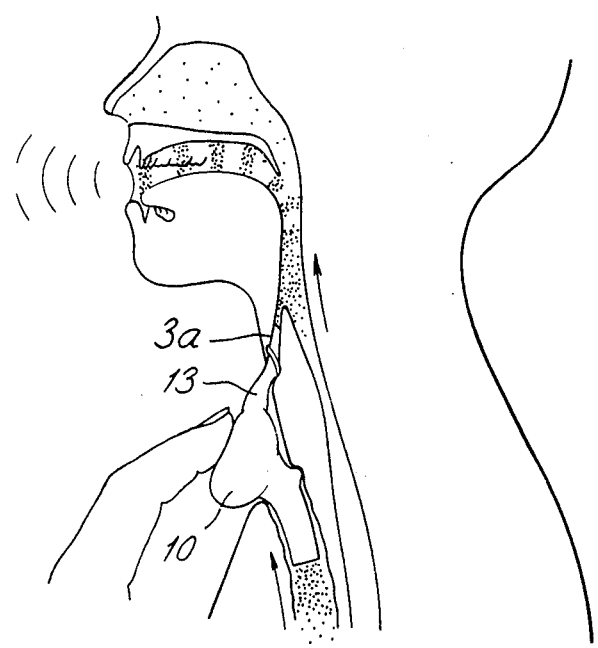

United States Patent [19]

Edwards

[11] 4,060,856
[45] Dec. 6, 1977

[54] SURGICAL USE OF A LARYNGEAL PROSTHESIS

[75] Inventor: Nigel Edwards, Bristol, England

[73] Assignee: National Research Development Corporation, London, England

[21] Appl. No.: 763,697

[22] Filed: Jan. 28, 1977

Related U.S. Application Data

[63] Continuation of Ser. No. 554,125, Feb. 28, 1975.

[30] Foreign Application Priority Data

Mar. 1, 1974 United Kingdom ................ 9345/74

[51] Int. Cl.$^2$ ................................................ A61F 1/20
[52] U.S. Cl. .................................................... 3/1.3
[58] Field of Search ............................. 3/1.3; 128/351

[56] References Cited

U.S. PATENT DOCUMENTS

| | | | |
|---|---|---|---|
| 2,804,076 | 8/1957 | Giraudon | 128/351 |
| 3,263,684 | 8/1966 | Bolton | 128/351 |
| 3,747,127 | 7/1973 | Taub | 3/1.3 |

FOREIGN PATENT DOCUMENTS

| | | | |
|---|---|---|---|
| 1,207,144 | 8/1959 | France | 128/351 |

OTHER PUBLICATIONS

"Extirpation of the Larynx" by David Foulis, Scientific American, Supplement No. 115, Mar. 16, 1878, pp. 1834 & 1835.

"The Artificial Larynx" by Yvan Lebrum, Published by Swets & Zeitlinger, B.V. – Amsterdam, 1973, pp. 53–56.

Primary Examiner—Ronald L. Frinks
Attorney, Agent, or Firm—Cushman, Darby & Cushman

[57] ABSTRACT

A patient subjected to laryngectomy is provided surgically with a fistula intended to serve as a pseudo-glottis, and a tracheostome, these two tracts being sited in the midline region of the neck surface. A laryngeal prosthesis for the patient is of generally symmetrical form comprising a hollowed main body with two external tubes to respectively engage the surgically-formed tracts, the fistular tube being sufficiently short to avoid inhibiting the pseudo-glottis function. The prosthesis body is apertured to provide a valve function communicating the tracheal tube with atmosphere for respiration, or with the fistular tube for phonation. This function can be effected by a normally-open flap valve closable by a first high pressure in the body, and a normally-closed blow-out valve may then be appropriate to open at second higher pressure to remove secretions, together with a further normally-open valve to close the fistular tube at the higher pressure. Also, a non-return valve is normally appropriate in the fistular tube, and this, or a similar valve, can serve as a tone generator if necessary.

2 Claims, 6 Drawing Figures

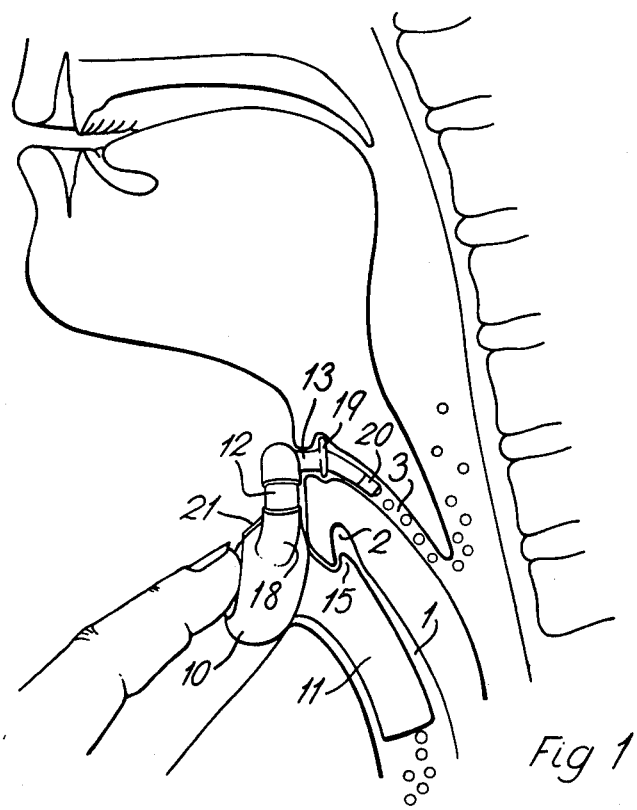
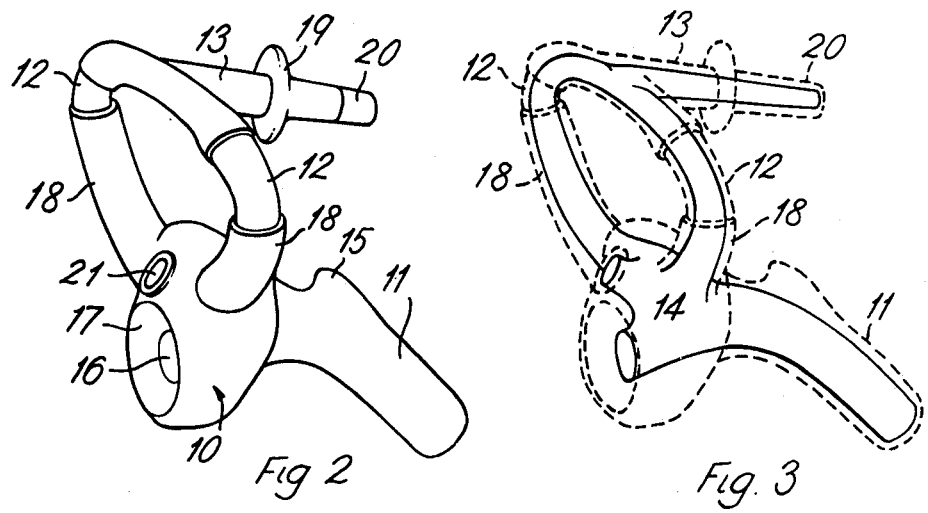

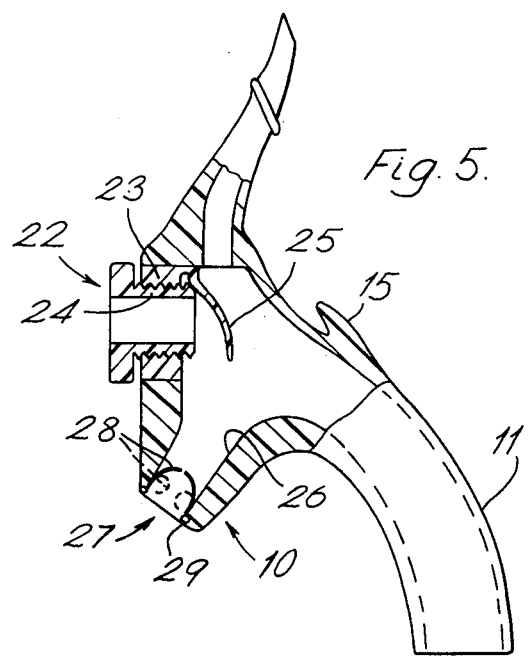
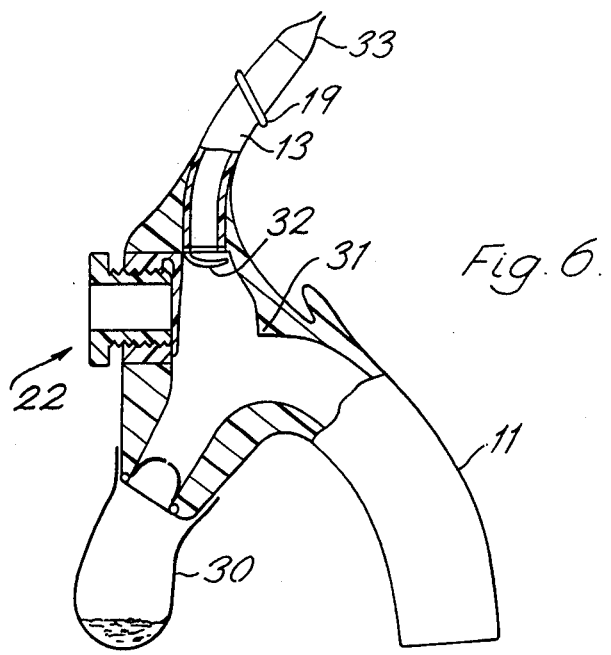

SURGICAL USE OF A LARYNGEAL PROSTHESIS

This is a continuation, of application Ser. No. 554,125 filed Feb. 28, 1975.

This invention concerns laryngeal prostheses for voice restoration following total laryngectomy.

Conventionally, such restoration has been offered by the oesophogeal speech method but this affords adequate speech communication for only a minority of patients and, even then, is not satisfactory in so far as it is difficult to learn, unphysiological by dissociation of respiratory action from phonation, and unnatural in quality.

Some of the failures with the oesophageal method have used various forms of externally applied vibration, but none of these forms have proved generally satisfactory or acceptable.

Recently, interest has been shown in proposals for developing alternative and more physiological alaryngeal speech by diverting the patient's expired air from the trachea into the pharynx by way of a tracheopharyngeal shunt involving use of an external prosthesis. The prosthesis of such a proposal normally comprises a hollowed body which is apertured to provide a valve function and to communicate with a tracheal tube and fistular tube connected with the body, the valve function allowing direct communication of the tracheal tube, through the body, to atmosphere for purposes of respiration, or communication of the tracheal tube, through the body, with the fistular tube for purposes of phonation. However, the few proposals in question involve the provision of a fistula to one side of the patient's midline, which fistula enters the oesophagus below the cricopharangeal sphincter, with the intention of having a pseudo-glottis at cricopharangeal level as in the oesophageal speech method. This off-set location of the fistula can be regarded as a risk to the vascular channels in the neck, and location of the pseudo-glottis in the cricopharangeal region, or elsewhere in the larynx for that matter, is likely to produce some of the undesirable quality of phonation of the oesophageal method.

An object of the present invention is to improve this situation and, to this end, the invention involves changes in both the surgical and prosthetic aspects of the prior proposals. More particularly, the invention involves the provision of a generally midline fistula and location of the pseudo-glottis in the fistula itself. This leads to the provision of a prosthesis which is of generally symmetrical form and which comprises a fistular tube which is short, relative to the associated tracheal tube, to avoid inhibiting the desired pseudo-glottis function.

These and other features of the invention will be more fully described, by way of example, with reference to the accompanying drawings, in which:

FIG. 1 schematically illustrates the surgical preparation in a patient to receive a first prosthesis embodiment which is shown located in the patient;

FIGS. 2 and 3 respectively illustrate this first embodiment in a more detailed external view and in internal form;

FIG. 4 is similar to FIG. 1 in respect of a second prosthesis embodiment;

FIG. 5 diagrammatically illustrates a third prosthesis embodiment; and FIG. 6 diagrammatically illustrates a modification of FIG. 5.

FIG. 1 indicates the general nature of the surgical preparation for use of the prosthesis of FIGS. 2 and 3, which preparation comprises the provision of a tracheostome 1 fashioned with a superior recess 2, and the formation of a pharyngocutaneous fistula 3 of mucous membrane about four centimeters above the tracheostome, both the tracheostome and fistula being substantially in the midline relative to the neck skin surface. The fistula is intended to provide a pseudo-glottis. While this preparation can be effected after laryngectomy, it is preferred that the preparation be effected as part of a one-stage surgical reconstruction at the time of laryngectomy to avoid the prolonged nature and healing of, and the increased risk of complications in, multistage surgery.

Turning to the relevant prosthesis: in its general form this comprises a hollowed and apertured main body 10 with which a tracheal tube 11 and two connector tubes 12 directly communicate, the connector tubes 12 each communicating at the end further from the body 10 with a fistular tube 13. As shown by FIG. 1, the tracheal and fistular tubes 11 and 13 respectively engage in the tracheostome 1 and fistula 3, with the body 10 and tubes 12 remaining outside the patient, to form a substantially symmetrical arrangement. Also, it will be noted that the fistular tube is short so as to project only partway into the fistula, while the tracheal tube is longer to project substantially into the tracheostome.

The body 10 has a hollow 14 which opens into five separate apertures which are located, relative to the disposition of the body when in use as shown by FIG. 1, one at the rear of the body, one at the front of the body, two at respectively opposite locations between the sides and top of the body, and one between the front and top of the body.

The first of these apertures is communicated with the lumen of the tracheal tube 11, this tube being suitably connected to the body to extend rearwardly and downwardly therefrom. The tube 11 has a projection 15 partway therealong from its upper surface, which projection is tapered towards the free end of the tube 11 while having a sharper or undercut inclination at its end nearer the body 10. This projection engages the tracheal recess 2 during use of the prosthesis to act against undesired dislodgement of the tracheal tube. Also, while the tube 11 should be of sufficiently firm construction to allow its engagement in the tracheostome without collapse of its lumen, the tube should be sufficiently distensible to afford a substantial air-tight fit between the tube and the tracheostome wall in response to increase of intratracheal pressure during phonation.

The second aperture of the body 10 is denoted at 16 and opens into the central region of a depression 17. This aperture can be closed by a finger to divert air flow from the tracheostome, which flow is otherwise expired through the aperture. This diversion function can alternatively be effected by a valve as discussed hereinafter.

The third and fourth apertures of the body 10 are defined by respective tubular extensions 18 integrally formed with the body 10 to extend upwardly and laterally outwardly therefrom. These extensions are individually connected by way of the connector tubes 12 to the fistular tube 13. For this purpose the tube 13 is formed to T-shaping with the tubes 12 being connected to the opposite ends of the bar of this shape, and the stem of the T-shape being engageable in the fistula 1. The major portion of the tube 13, like the tube 11, is of firm construction but has some elasticity.

Additional features of the fistular tube comprise a stiff annular flange 19 formed around the stem partway therealong sealingly engaging the stem against the fistular wall against leakage so that, when the device is in use, this flange forms and sealingly engages in a recess in the fistular wall to inhibit leakage of saliva and ingested material between the wall and the stem of the tube 13.

Also, the free end of the fistular tube stem is in the form of a thin walled, normally collapsed, tubular one-way valve 20 which serves to prevent undesired reflux of saliva, but opens in response to expired air pressure in the tube when the aperture 16 is closed to sealingly engage the fistular wall and to pass diverted air to the pharynx for phonation. The valve 20 is longitudinally stiffened by a suitable member to facilitate insertion into the fistula.

The remaining aperture in the body 10 also forms part of a one-way valve 21 by the provision of a flap which is biased to normally close the aperture, but moves to open the aperture for purposes of inspiration when the aperture 16 is closed.

This prosthesis embodiment has been made from a silicone material and has been used clinically with some degree of success. However, development of the invention has continued with a view to effecting a greater improvement relative to the prior proposals.

One area for improvement is seen to be in the surgical reconstruction. Initially this reconstruction provided a fistula sloping downwardly to meet the pharynx at cricopharangeal level as shown in FIG. 1. Study of pharangeal motility and pressure patterns now indicates that advantage is gained with a fistula 3a sloping upwardly from the neck skin surface just below the tongue base as shown in FIG. 4. This reduces the possibility of leakage between the fistular tube and fistular wall compared to a downwardly sloping fistula, and may make possible the provision of a voluntarily controlled sphincter mechanism. FIG. 4 also shows a modification in the prosthesis in that the fistula tube 13 is connected directly with the body 10. It may be appropriate also to provide the fistular tube with a flange, and surgically form a recess in the fistula to receive the same in similar manner to that for the tracheal tube.

Further improvement can also be made to the prosthesis by the provision, as noted above, of a valve to effect the air flow diversion at aperture 16 in the body 10. Clearly such a valve can be of manually operable form to open and close the aperture dependent upon whether simple respiration or phonation is required. This offers advantage over the need for the patient to maintain one of his arms in a given attitude for the purposes of obturation of the aperture by a finger during phonation. Alternatively, and preferably for most circumstances, a valve can be provided which operates automatically from a normally open state to close the aperture for purposes of phonation. Such a valve can be of any suitable form which closes in response to a predetermined level of intratracheal pressure on the basis that phonation is normally associated with a higher pressure than is simple respiration. It may, in addition, be preferable that such an automatic valve automatically opens once more in response to a yet higher predetermined level of pressure to serve for the removal of secretions, as with coughing, and expulsion of excess air. It will be usually more expedient in practice to provide these automatic valve functions by way of two separate valves of respectively normally open form for respiration/phonation modes of operation and normally-closed form for highest pressure operation mode, but it may be possible to provide an integrated valve structure for these purposes.

FIG. 5 illustrates a third prosthesis embodiment which is generally similar to that of FIG. 4 but incorporates examples of two separate valves as just discussed. The first of these valves is denoted generally at 22 and is located in the site of aperture 16. The valve 22 comprises a first tubular valve body part 23 which is secured in the aperture site and is internally threaded to receive in longitudinally adjustable manner therein a correspondingly externally threaded second tubular valve body part 24. The valve body part 23 also carries at its inner end a flap 25 which extends across the inner ends of valve body parts, normally in spaced relation therefrom. The flap is resilient such that flow of air from the tracheal tube 11 will deflect the flap towards the valve body parts until the flap closes the latter parts at a substantially predetermined air pressure. This valve closure causes air to flow into the fistular tube 13 for phonation, and the pressure at which this occurs can be varied to suit a given patient by adjustment of the valve body part 24 to project closer to, or further from, the normal position of the flap.

The second valve of FIG. 5 involves the provision of an additional aperture 26 in the main body 10 of the prosthesis, which aperture serves to hold a tricuspid valve 27. Such valves have three resilient leaf-like parts 28 extending from an annular base 29 and can assume mutually contacting positions to close the opening in the base, or mutually separated positions exposing the base opening. In this instance the former position is shown in full outline in the drawing and is the normal position, while the open position is shown in broken outline and results from intertrachial air pressure at a high level, above that for phonation, as discussed above.

It will be appropriated for some purposes to associate a collector with this second valve to collect expelled secretions, and such a collector is shown in the form of a separable bag 30 connected to the exterior of body 10 around the aperture 26 in the modification of FIG. 6.

FIG. 6 also shows modification to the interior of body 10 by the provision of a baffle formation 31 to direct secretions from the tracheal tube towards the valve 27, and away from other valves to avoid interference with functioning of the latter.

Additionally FIG. 6 shows modification by the provision of a further valve 32, of flap form generally similar to valve 22, which is located adjacent the inner end of the fistular tube 13 connection with the body 10. This valve 32 avoids application of excessive pressure to the tube 13 and undesired phonation which may result therefrom.

Lastly in FIG. 6, the one-way valve 20 is replaced by (or augmented with) a normally-closed tricuspid valve 33 in the lumen of the fistular tube, which valve 33 serves to inhibit leakage into the tube from above and can also function as a vibrator to add a mechanically-produced sound into the vocal tract if this is required.

I claim:

1. The use of a laryngeal prosthesis for a laryngectomee, which prosthesis comprises a hollowed body having first and second tubes connected thereto, said body being apertured to provide a valve function allowing selective opening and closure of the hollow of said body relative to the exterior thereof, and which use comprises:

surgically forming in said laryngectomee a tracheostome sited in the midline region of the neck,
surgically forming in said laryngectomee a similarly sited fistula extending upwardly to a location adjacent the tongue base,
surgically forming a pseudo-glottis in the inner end portion of said fistula, and
respectively locating said tubes in said tracheostome and fistula with said body located outside the laryngectomy, said second tube being located only in the outer end portion of said fistula to avoid overlaying said pseudo-glottis, and said valve function serving to open said body to communicate said fistula with the external atmosphere for respiration and to close said body to communicate said tubes therethrough for phonation by activation of said pseudo-glottis.

2. A use according to claim 1 wherein at least one of said tubes has an outwardly extending flange, and the respective one of said tracheostome and fistula is surgically formed with a recess in which said flange is located.

* * * * *